United States Patent

Bonne et al.

[11] Patent Number: 6,079,253
[45] Date of Patent: Jun. 27, 2000

[54] METHOD AND APPARATUS FOR MEASURING SELECTED PROPERTIES OF A FLUID OF INTEREST USING A SINGLE HEATER ELEMENT

[75] Inventors: Ulrich Bonne, Hopkins; David Kubisiak, Chanhassen; Robert J. Matthys, St. Anthony; Spencer B. Schuldt, Bloomington, all of Minn.

[73] Assignee: Honeywell Inc., Minneapolis, Minn.

[21] Appl. No.: 09/002,156

[22] Filed: Dec. 31, 1997

[51] Int. Cl.$^7$ .................................................. G01N 25/00
[52] U.S. Cl. ..................... 73/61.76; 73/54.42; 374/43; 374/137; 702/50
[58] Field of Search ................ 73/61.74, 54.42, 73/61.76, 53.01, 54.43; 374/43, 139, 137; 702/50, 136

[56] References Cited

U.S. PATENT DOCUMENTS

| | | | |
|---|---|---|---|
| 3,015,232 | 1/1962 | Schnoll | 73/204 |
| 3,335,606 | 8/1967 | Scarpa | 73/204 |
| 4,279,147 | 7/1981 | Djorup | 73/189 |
| 4,501,144 | 2/1985 | Higashi et al. | 73/204 |
| 4,576,050 | 3/1986 | Lambert | 73/861.05 |
| 4,682,503 | 7/1987 | Higashi et al. | 73/755 |
| 4,713,970 | 12/1987 | Lambert | 73/861.05 |
| 4,735,082 | 4/1988 | Kolloff . | |
| 4,944,035 | 7/1990 | Aagardl et al. . | |
| 4,961,348 | 10/1990 | Bonne | 73/861.02 |
| 5,150,611 | 9/1992 | Kleinhans | 73/204.14 |
| 5,184,509 | 2/1993 | Kienzle et al. | 73/204.14 |
| 5,193,388 | 3/1993 | Kleinhans | 73/204.14 |
| 5,237,523 | 8/1993 | Bonne et al. | 364/571.03 |
| 5,247,156 | 9/1993 | Favre | 219/209 |
| 5,303,167 | 4/1994 | Bonne | 364/556 |
| 5,379,630 | 1/1995 | Lacey . | |

FOREIGN PATENT DOCUMENTS

| | | |
|---|---|---|
| 0364982 | 4/1990 | European Pat. Off. . |
| 0419873 | 4/1991 | European Pat. Off. . |
| 0468793 | 1/1992 | European Pat. Off. . |
| 9206369 | 4/1992 | WIPO . |

OTHER PUBLICATIONS

Bonne et al., "Burstproof, Thermal Pressure Sensor for Gases", 1994 Solid State Sensor and Actuator Workshop, 2 pages.

Lambert et al., "An air flow sensor based on interface thermal wave propagation", *J. Appl. Phys.*, 59(1), Jan. 1986, 3 pages.

Bonne et al., "Natural Gas Flow and Property Sensor", *GRI Engine Technology Advisory Committee Meeting*, May 1996, 5 pages.

Healy et al., "The Theoery of the Transient Hot–Wire Method for Measuring Thermal Conductivity", *Physics*, 82C (1976) pp. 392–408.

Protodyanakonow et al., "The Use of Probes in Investigating Two–Phase Flow", *Fluid Mech., Soviet Res.*, 12, No. 3, (May–Jun. 1983), pp. 98–157.

Carslaw et al., "Conduction of Heat in Solids", $2^{nd}$ Edition, Clarendon Press, Oxford, UK (1959), 7 pages.

Mylroi, "Cross–Correlation Flow Measurement Systems", *G.B.*, 12, No. 6–7, 1977, 4 pages.

Kubisiak et al, "Microamemometer–Based Gas Flow Sensing", *IGT Symposium of Natural Gas Quality Measurement*, Jul. 1990, 18 pages.

*Primary Examiner*—Hezron Williams
*Assistant Examiner*—Thuy Vinh Tran
*Attorney, Agent, or Firm*—Ian D. MacKinnon

[57] ABSTRACT

A method and apparatus for determining selected fluid properties including thermal conductivity, pressure and/or temperature using a single heater element of the sensor, and in a relatively short period of time. This is accomplished by measuring a variable phase or time lag between an input signal provided to the heater element and a subsequent transient temperature response of the heater element.

35 Claims, 14 Drawing Sheets

PRIOR ART

METHOD AND APPARATUS FOR MEASURING SELECTED PROPERTIES OF A FLUID OF INTEREST USING A SINGLE HEATER ELEMENT

CROSS REFERENCE TO CO-PENDING APPLICATIONS

The present application is related to U.S. patent application Ser. No. 09/001,530, filed Dec. 31, 1997, entitled "TIME LAG APPROACH FOR MEASURING THERMAL CONDUCTIVITY AND SPECIFIC HEAT", U.S. patent application Ser. No. 09/002,157, filed Dec. 31, 1997, entitled "TIME LAG APPROACH FOR MEASURING FLUID VELOCITY", U.S. patent application Ser. No. 09/001,735, filed Dec. 31, 1997, entitled "SELF-OSCILLATING FLUID SENSOR", and U.S. patent application Ser. No. 09/001,453, filed Dec. 31, 1997, entitled "FLUID PROPERTY AND FLOW SENSING VIA A COMMON FREQUENCY GENERATOR AND FFT", which are all assigned to the assignee of the present invention and incorporated herein by reference.

BACKGROUND OF THE INVENTION

1. Field of the Invention

The present invention relates to the measurement of certain physical properties of fluids and, more particularly, to the determination of the thermal conductivity, pressure and/or temperature of fluids.

2. Description of the Prior Art

A number of approaches have been devised to measure the thermal conductivity and other properties of a fluid of interest. One such approach is described in U.S. Pat. No. 4,735,082 in which thermal conductivity is detected using a Wheatstone bridge technique in which a filament in one leg of the bridge is placed or positioned in a cavity through which the sample gas of interest is passed. The filament is used to introduce a series of amounts of thermal energy into the fluid of interest at various levels by varying the input voltage which, are, in turn, detected at another leg as voltage difference signals. Integration of the changes of the value of the successive stream of signals yields a signal indicative of the heat dissipation through the fluid, and thus, the thermal conductivity of the fluid.

Further to the measurement of thermally induced changes in electrical resistance, as will be discussed in greater detail below, especially with reference to prior art FIGS. 1–5, very small and very accurate "microbridge" semiconductor chip sensors have been described in which etched semiconductor "microbridges" are used as heaters and sensors. Such sensors might include, for example, a pair of thin film sensors around a thin film heater for measuring flow rates. Semiconductor chip sensors of the class described are treated in a more detailed manner in one or more of patents such as U.S. Pat. No. 4,478,076, U.S. Pat. No. 4,478,077, U.S. Pat. No. 4,501,144, U.S. Pat. No. 4,651,564, and U.S. Pat. No. 4,683,159, all of common assignee with the present invention.

One interesting approach to measuring the thermal conductivity, k, of a fluid using a microbridge structure is disclosed in U.S. Pat. No. 4,944,035 to Aagard et al. Aagard et al. discloses using a heater film and at least one spaced sensor films to measure the thermal conductivity, k, of the fluid of interest. The heater film is energized for a relatively long period of time so that the temperature of the fluid, and thus the spaced sensor or sensors, reach and maintain a relatively constant value. During this time, one or more Wheatstone bridge structures incorporating the sensor or sensors provides an output signal that represents the voltage imbalance caused by the temperature change in the microbridge sensor or sensors. The amplitude of this imbalance is related to the thermal conductivity, k, of the fluid as shown specifically in FIG. 13 of Aagard et al. Using previously derived calibration data, the thermal conductivity can thus determined.

A limitation of this approach is that both a heater element and at least one sensor element are required to measure the thermal conductivity of a fluid. Another limitation is that relatively long heater pulses are required to allow the temperature of the spaced sensor element to reach and maintain a constant value. Thus, it would be desirable to provide a sensor that can determine the thermal conductivity, k, and other fluid properties, in a relatively short period of time using only one element such as a heater element.

SUMMARY OF THE INVENTION

The present invention overcomes many of the disadvantages associated with the prior art by providing apparatus and method for determining selected fluid properties including thermal conductivity, pressure and/or temperature using a single heater element, and in a relatively short period of time. This is accomplished by measuring a variable phase or time lag between an input signal provided to the heater element and a subsequent transient temperature response of the heater element.

In a preferred embodiment, a periodic time-varying input signal is provided to the heater element, and the heater element is disposed in and closely coupled to a fluid medium (gas or liquid) of interest. The input signal provides power to the heater element and induces a transient elevated temperature condition in the heater element and the fluid of interest. Because the heater element is closely coupled to the fluid medium, the thermal conductivity "k" directly affects the time variable temperature response of the heater element. Further, the thermal conductivity of a fluid is typically dependent on the pressure and/or temperature of the fluid. Thus, it has been found that the thermal conductivity, pressure and/or temperature of the fluid of interest can be determined by examining a variable phase lag or time lag between the input signal provided to the heater element and a subsequent transient temperature response of the heater element.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
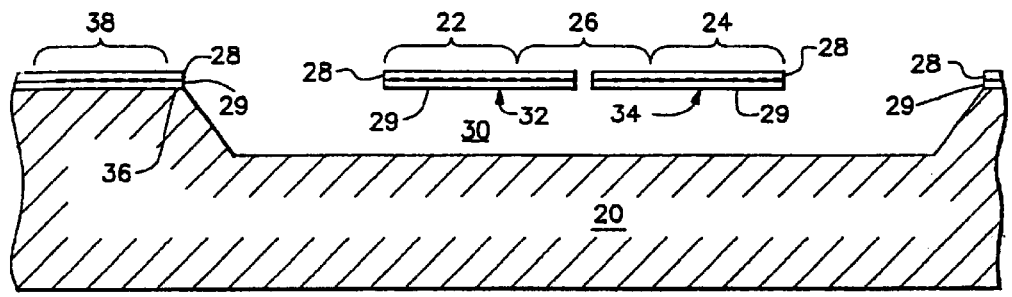
FIGS. 1, 2 and 3 are different views of a prior art embodiment of a microbridge flow sensor.

The present invention, then, is directed to a system which enables the determination of selected fluid properties such as thermal conductivity, pressure and/or temperature using a single heater element. The preferred embodiments of the approach contemplate disposing a microscopic sized heating element in a relatively static (zero flow) sample of the fluid of interest. The microsensor system or "microbridge", as it will be referred to herein, though not limiting, is presently preferred for several reasons. The system is extremely fast-reacting, is very accurate, very sensitive because of its advantageous coupling to the fluid of interest and small and adaptable to a variety of configurations.

The microbridge semiconductor chip sensor contemplated, for example, in certain embodiments preferred for the invention may resemble the form of one or more of the microbridge systems illustrated in the patents identified above. Such a system is exemplified by FIGS. 1–5 taken from U.S. Pat. No. 4,994,035 to Aagard et al. A discussion of that example will now be presented as it will be helpful in understanding the present invention. While the present discussion is believed sufficient, to the extent necessary, any additional material contained in the microbridge related patents cited is deemed to be incorporated herein by reference.

The prior art system of FIGS. 1–5 contemplates a pair of thin film temperature sensors 22 and 24, a thin film heater 26 and a support member 20 supporting the sensors and heater out of contact with the base substrate. Sensors 22 and 24 are disposed on opposite sides of heater 26. Support member 20 is a semiconductor, preferably silicon, chosen because of its adaptability to precision etching techniques and ease of electronic chip producibility. The embodiment includes two identical temperature sensing resistor grids 22 and 24 acting as the thin film heat sensors and a centrally located heater resistor grid 26 acting as the thin film heater.

Sensors 22 and 24 and heater 26 may be fabricated of any suitable, stable metal or alloy film. The metal used may be a nickel-iron alloy sometimes referred to as permalloy, with a composition of 80 percent nickel and 20 percent iron. The sensor and heater grids are encapsulated in a thin film of dielectric, typically comprising layers 28 and 29 and preferably silicon nitride, $Si_3N_4$ to form the film members.

Figure 2:
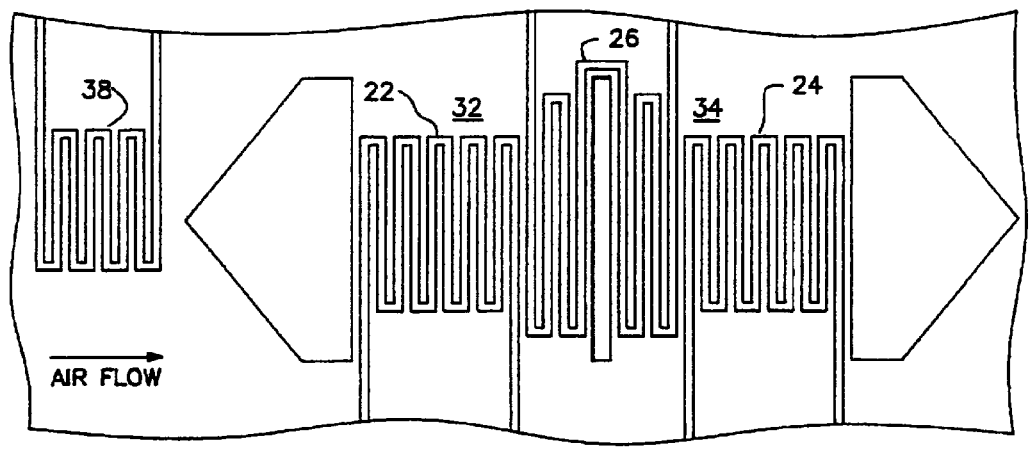

In the FIGS. 1 and 2, the sensor comprises two thin film members 32 and 34, with member 32 comprising sensor 22 and member 34 comprising sensor 24, each member comprising one-half of heater 26 and having a preferred dimension of 150 microns wide and 400 microns long.

The system further describes an accurately defined fluid space 30 that effectively surrounds elements 22, 24, 26, and is achieved by fabricating the structure on silicon surface 36. Thin film elements 22, 24 and 26 have thicknesses of approximately 0.08 to 0.12 micron with line widths on the order to 5 microns and spaces between lines on the order of 5 microns. The elements encapsulated in the silicon nitride film preferably have a total thickness of approximately 0.8 microns or less. The fluid space 30 may be fabricated by subsequently etching an accurately defined fluid space of about 100 microns deep into silicon body 20 beneath members 32 and 34.

Figure 3:
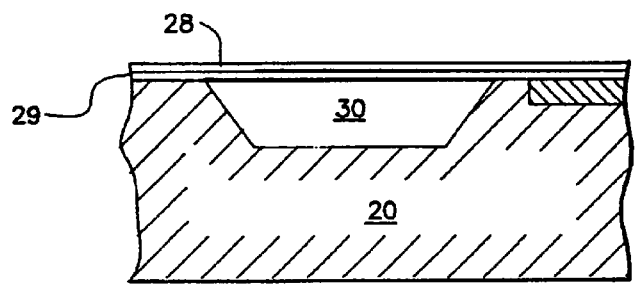

Members 32 and 34 connect to top surface 36 of semiconductor body 20 at one or more edges of depression or fluid space 30. As illustrated in FIG. 3, members 32 and 34 may be bridged across depression 30; alternately, for example, members 32 and 34 could be cantilevered over depression 30.

In the system shown, heat flows from the heater to the sensor by means of both solid and fluid couplings therebetween. Of note is the fact that silicon nitride ($Si_3N_4$), besides being a good electrical insulator, is also an effective solid thermal insulator. Because the connecting silicon nitride film within members 32 and 34 is a good insulator, heat transmission through the solid does not dominate the propagation of heat from heater 26. This further enhances the relative amount of the heat conducted to sensing resistors 22 and 24 from heater resistor 26 by flow through the surrounding fluid rather than through the supporting nitride film. Moreover, the supporting silicon nitride film has a low enough thermal conductivity that sensing resistor grids 22 and 24 can be located immediately adjacent or juxtaposed to heating resistor grid 26. Thus, sensing resistor grids 22 and 24 are in effect suspended rigidly in the fluid space proximate heater resistor 26 and act as thermal probes to measure the temperature of the air near and in the plane of heater resistor grid 26.

Figure 4:
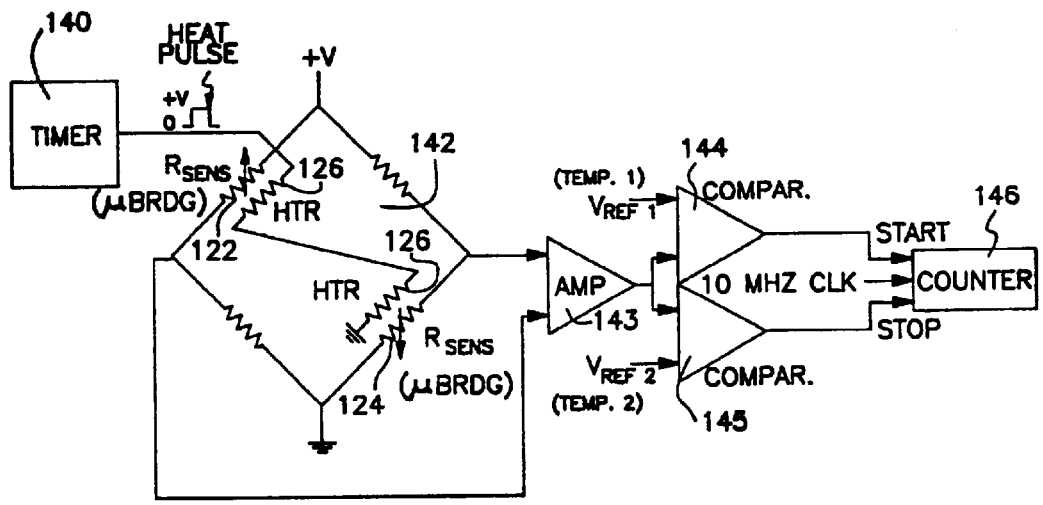
FIGS. 4 and 5 are typical circuits for use with the sensors of FIGS. 1–3 to determine the thermal conductivity of a fluid of interest.

The operation of the system in sensing thermal conductivity and specific heat is described in detail in the above-referenced U.S. Pat. No. 4,994,035 to Aagard et al. Typical circuit implementation is discussed briefly with reference to FIGS. 4 and 5 to add some insight. FIG. 4 shows a pulse generator 140 providing square-wave electrical pulses to the heater 126. The heater couples the heat pulse to the sensors 122 and 124 in the bridge 142, primarily through the fluid. The output of the bridge is connected through an amplifier 143 to a pair of comparators 144 and 145 which operate "start" and "stop" inputs to a counter 146 which counts 10 MHz clock pulses. The counter measures the time interval between two reference temperatures $T_2$ and $T_1$ at sensors 122 and 124.

Figure 5:
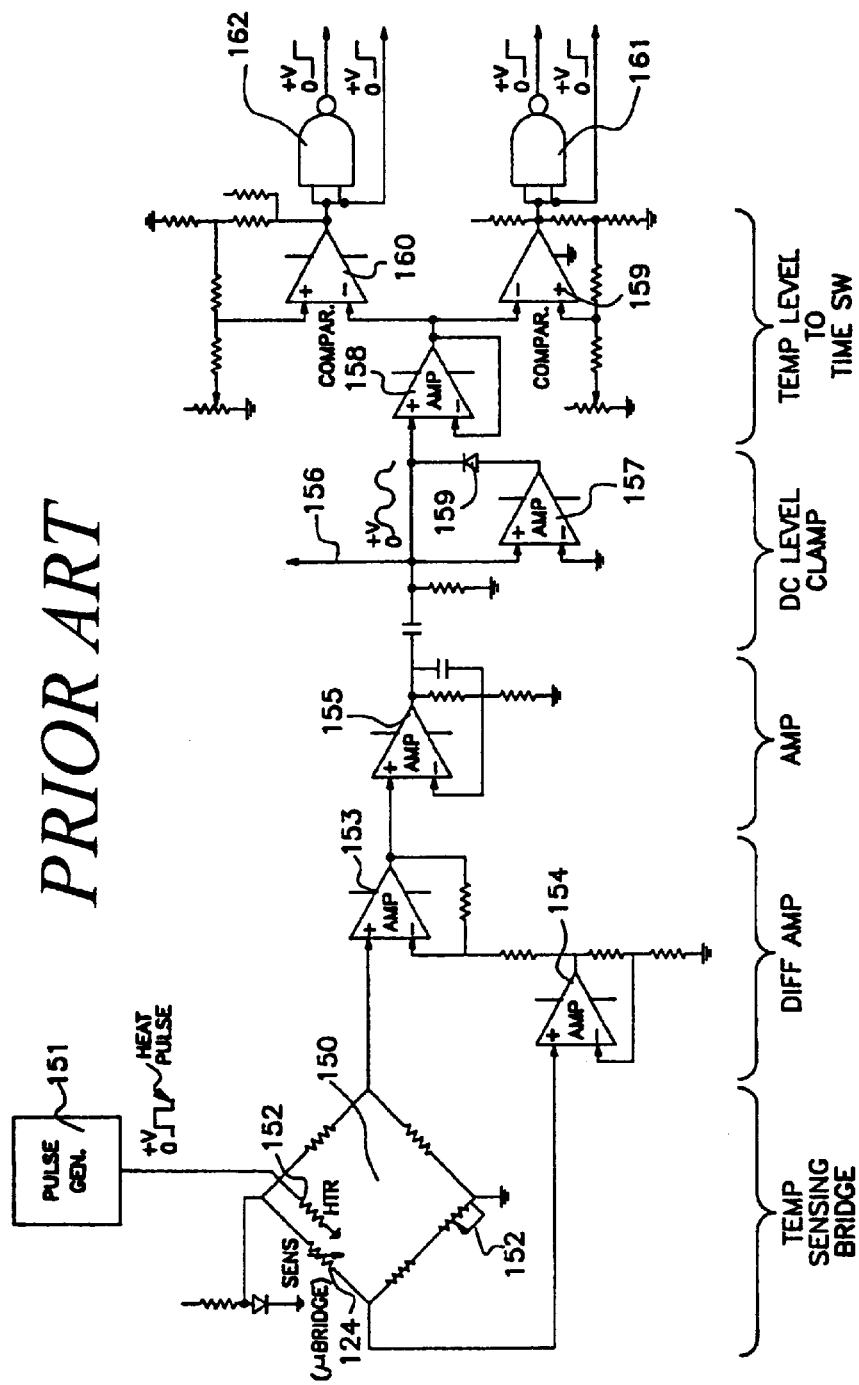

FIG. 5 is similar to FIG. 4, but provides more detail. The bridge configuration is a heater-space-sensor configuration. The sensor resistance arm of the microbridge is set into a Wheatstone bridge 150 at 124. Another proximate resistive arm 122 is fed a voltage pulse from pulse generator 151 to provide a heat pulse into a microbridge element 126. The Wheatstone bridge 150 also may contain a nulling balancing resistor 152 which can be used to initially zero the device.

The microbridge resistor sensor 124 in the Wheatstone bridge receives the heat pulse from heater element 122 principally by thermal conduction through the surrounding fluid. Some conduction of course, does occur through the solid microbridge substrate and surroundings.

The circuitry of FIG. 5 is conventional and can readily be explained with reference to its functional operation with regard to processing the bridge output signal. The voltage output signals of the bridge 150 are amplified by differential amplifiers 153 and 154 in a differential amplifier section. The balance signal is further amplified by a high gain amplifier at 155. The signal at 156 as is the case with the signal at 147 in FIG. 4 is in the form of a DC voltage signal, U, the amplitude of which is solely related to the thermal conductivity of the fluid of interest as discussed above.

The remainder of the circuitry of FIG. 5 includes a DC level clamping amplifier 157 and isolation amplifier 158. The temperature level, time-related switching and counting circuitry includes comparators 159 and 160 together with Nand gates 161 and 162 having outputs which are connected to the counter timing device (not shown) as in FIG. 4. The output signal from the Wheatstone bridge, U, represents the voltage imbalance caused by the temperature change in microbridge sensor or sensors induced by the corresponding heater pulse output. Because the magnitude of this imbalance is related directly to the amount of energy absorbed by the sensor or sensors, the amplitude of the signal is directly related to the thermal conductivity, k. Using previously derived calibration data, the thermal conductivity of an unknown fluid can thus be determined.

By measuring the time needed for the sensor temperature to rise or fall between two or more known reference temperature values or markers as represented by sensor resistance or bridge voltage outputs, and by knowing k, a measure related to the specific heat per unit volume, $c_{pv}$, of the fluid of interest is obtained. The timing device may be a conventional 10 MHZ pulse counter or the like.

A limitation of determining thermal conductivity, k, in the above-described manner is that both a heater element and at least one sensor element are required. Another limitation is that relatively long heater pulses are required to allow the temperature of the spaced sensor element to reach and maintain a constant value. Finally, the amplitude of the resistance change in the sensor elements may affect the measured thermal conductivity value. It is known that the resistance of many metals may vary over time, at least to some degree, adding an additional potential error source.

Figure 6:
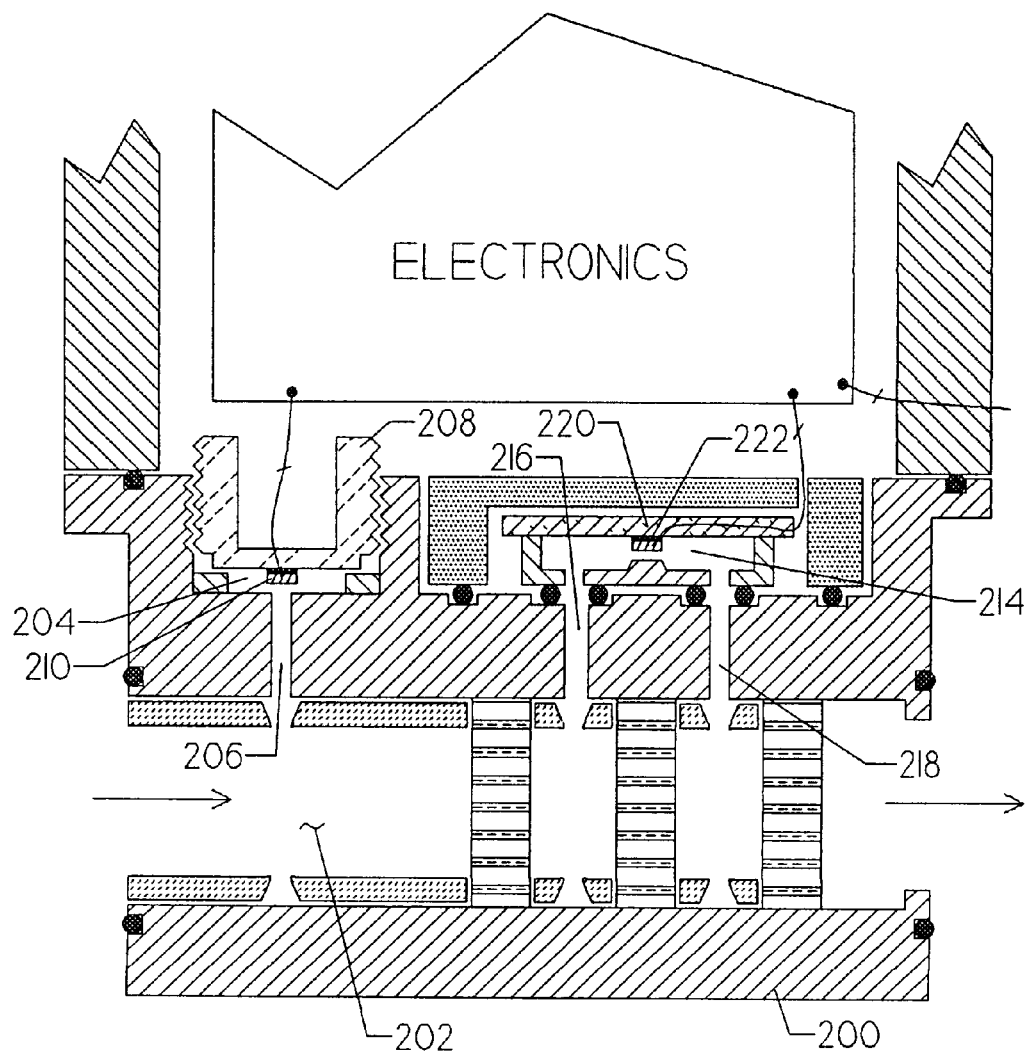
FIG. 6 is partial cut-away view of a microbridge sensor package.

FIG. 6 is a partial cut-away view of a microbridge sensor package placed in line with a flow pipe. The main flow channel 200 having a central bore 202 is connected to the pipe that carries a fluid of interest. A first chamber 204 is in fluid communication with the central bore 202 of the flow channel 200 via a single bore 206. A header 208 having a first microbridge sensor 210 mounted thereto is inserted into the first chamber 204 and secured to the main flow channel 200 as shown. In this configuration, the first microbridge sensor is exposed to the fluid of interest with substantially zero flow. The first microbridge sensor 210 is typically used to measure fluid properties such as thermal conductivity, specific heat, temperature and pressure.

A second sensor 222 is positioned in a small bypass channel 214. In this configuration, the second microbridge sensor is exposed to the flow of the fluid of interest. The second microbridge sensor 222 is typically used to measure fluid velocity.

Figure 7:
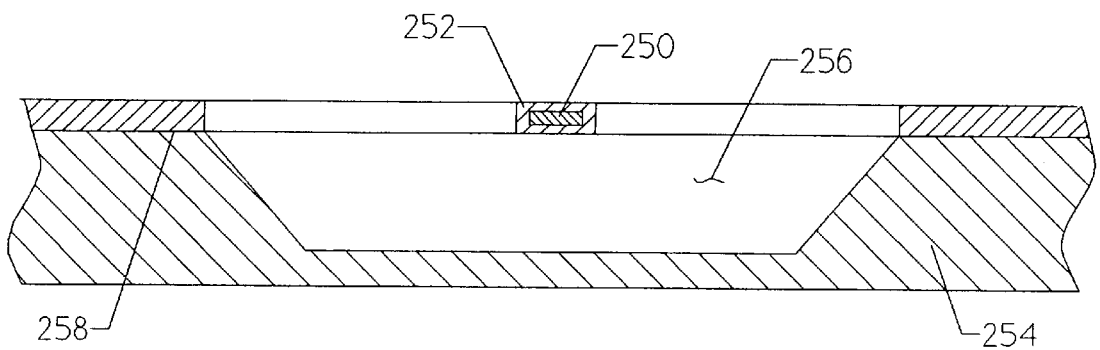
FIG. 7 is an illustrative cross sectional view of a microbridge in accordance with the present invention.

FIG. 7 is an illustrative cross sectional view of a microbridge system in accordance with the present invention. As indicated above, the present invention provides apparatus and methods for allowing accurate determination of selected fluid properties including thermal conductivity, pressure and temperature using a single heater element. The single heater element is shown at 250. A support member 252 supports the heater element out of contact with the base substrate 254. Together, the heater element 250 and support member 252 form a film member.

Heater element 250 may be fabricated of any suitable, stable metal or alloy such as platinum, Nickel, Iron-Nickel, etc. Further, heater element 250 may be any resistive element including a wire, but is preferably a film. Finally, heater element 250 may take on any shape including a grid pattern as described above, or simply a line. As indicated above, the heater element 250 is preferably encapsulated in a thin film of dielectric, such as silicon nitride, $Si_3N_4$, to form the support member 252.

An accurately defined fluid (gas or liquid) space 256 is preferably provided which effectively surrounds heater element 250, and is achieved by fabricating the structure on silicon surface 258. Heater element 250 preferably has a thickness of approximately 0.08 to 0.12 micron, with a line width on the order to 5 microns and, if a grid is used, spaces between lines on the order of 5 microns. The fluid space 256 may be fabricated by subsequently etching an accurately defined silicon-free space of about 100 microns deep into silicon substrate 254 beneath heater element 250.

Support member 252 and heater element 250 preferably connect to top surface 258 of semiconductor substrate 254 at one or more edges of etch pit or depression 256. Support member 252 and heater element 250 may be bridged across depression 256 as shown, or alternately, for example, cantilevered over depression 256. It is recognized that any number of heater and sensor elements may be provided adjacent heater element 250. However, for illustration purposes, only one heater element has been shown.

Figure 8:
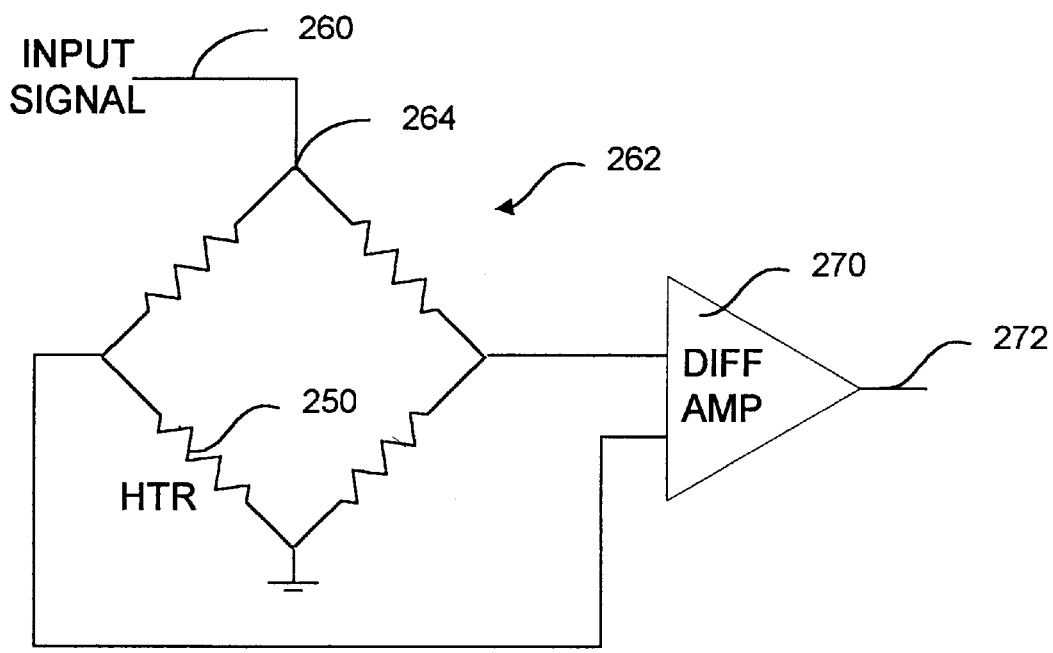
FIG. 8 is a schematic diagram of an illustrative circuit for use with the microbridge heater element of FIG. 7.

FIG. 8 is a schematic diagram of an illustrative circuit for use with the microbridge heater element of FIG. 7. In accordance with the present invention, a periodic time-varying input signal 260 is provided to a heater element 250 that is disposed in and closely coupled to a fluid medium (gas or liquid) of interest. To simultaneously provide power to, and measure the resistance response of the heater element 250, the heater element 250 is shown incorporated into one leg of a Wheatstone bridge 262. The time varying input signal 260 is provided to a power input terminal 264 of the Wheatstone bridge 262, which is either directly or indirectly coupled to the heater element 250 as shown. In this configuration, the Wheatstone bridge 262 provides a differential output signal that has an amplitude that is proportional to the resistance of the heater element 250. Preferably, the differential output signal is provided to a differential amplifier circuit 270 to provide an amplified output signal 272.

The input signal 260 provides power to the heater element 250 and inducing a transient elevated temperature condition in the heater element 250 and the fluid of interest. Because the heater element 250 is closely coupled to the fluid, the thermal conductivity, k, of the fluid directly affects the time variable temperature response of the heater element 250. Further, the thermal conductivity of the fluid is typically dependent on the pressure and/or temperature of the fluid. Thus, it has been found that the thermal conductivity, pressure and/or temperature of the fluid of interest can be determined by examining a variable phase lag or time lag between the input signal 260 provided to the heater element 250 and a subsequent transient temperature response of the heater element 250.

Figure 9:
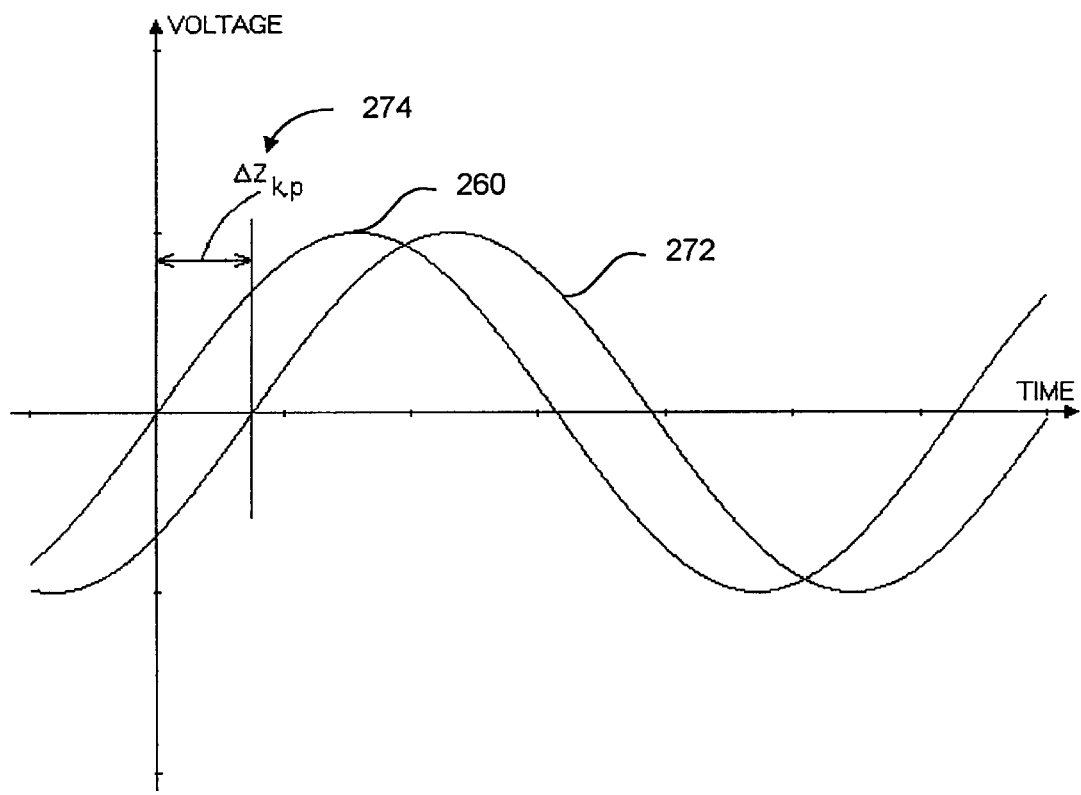
FIG. 9 is a timing diagram showing the measurable phase lag or lag time $\Delta z_{k,p}$ at zero crossing between the input signal provided to the heater element and the resulting resistance change of the heater element.

FIG. 9 is a timing diagram showing the desired lag time $\Delta z_{k,p}$ between the input signal 260 provided to the heater element and the resulting resistance change of the heater element 272 (see FIG. 8). The amplified output signal 272 lags the input signal by an amount that is proportional to the thermal conductivity of the fluid of interest, assuming the temperature and pressure of the fluid are fixed. The time lag $\Delta z_{k,p}$ is shown at 274.

Before providing the relation for determining the thermal conductivity of the fluid of interest from the time lag $\Delta z_{k,p}$, some background information is provided. The thermal dynamic interaction between the heater element 250 which is forced to experience fluctuating temperatures of:

$$T = T_0 + T_i \sin(\Omega z + \gamma) \qquad (1)$$

in response to a fluctuating input power $$P = P_0(1 + \sin(\Omega z)) \qquad (2)$$

can be described by a simple differential equation $$c_{pv} \, t \, dT/dz = P_0(1 + \sin(\Omega z)) - (h_1 + h_2)(T - T_f) - h_3(T - T_b) \qquad (3)$$

The meaning of the used symbols is as follows:

TABLE I

| Symbol | Nomenclature |
|---|---|
| f | frequency of the input signal, $H_z$ |
| ω | $2\pi f$, $H_z$ |
| $c_{pv}$ | specific heat per unit volume for the heater film and support member (10% Platinum, 90% $Si_3N_4$ Microbridge composite, $J/(cm^3 k)$ |
| t | heater film thickness, cm |
| T | sensor base temperature, with peak-to-peak amplitude of $2T_0$, k |
| $T_f$ | fluid temperature, k |
| $T_b$ | substrate temperature, k |
| $h_1$ | coefficient of conductive heat transfer to the fluid of interest (=$k/L_1$), $W/cm^3$ |
| $h_2$ | coefficient of forced convective heat transfer to the fluid of interest under laminar flow (=$k/L_2$), $W/cm^3$ |
| $h_3$ | coefficient of conductive heat transfer to the substrate, $W/cm^3$ |
| $L_1$ | characteristic length of thermal conduction from the heater element into the fluid phase, cm |
| $L_2$ | characteristic length of convective heat transfer, cm |
| z | time, s |
| Δz | time lag between input signal and the resistance of the heater means, s |
| γ | phase lag between input signal and the resistance of the heater means (γ = Δz · 2πf), radians |

Integration of equation (3) leads to the solution for the phase lag, γ, and the DC and AC signal amplitudes, $T_0$ and $T_1$, respectively as follows:

$$\gamma = \arctan(-2\pi f c_{pv} t/(h_1 + h_2 + h_3)) \qquad (4)$$

$$\Delta z = \gamma/(2\pi f) \qquad (5)$$

$$T_0 = ((h_1 + h_2)T_f + h_3 T_b + P_0)/(h_1 + h_2 + h_3) \qquad (6)$$

$$T_1 = P_0/((h_1 + h_2 + h_3)^2 + (c_{pv} t \Omega)^2)^{1/2} \qquad (7)$$

The contributions of $h_1$, $h_2$ and $h_3$ to the phase lag γ can be isolated and individually measured. During a calibration procedure, for example, the value of $h_3$ can be determined by subjecting the heater element to a vacuum condition, thereby reducing $h_1$ and $h_2$ to zero. A time lag value may then be measured between the input signal and the output signal of the heater element under the vacuum condition. The value of $h_2$ may then be calculated using the relation:

$$h_3 = -2\pi f c_{pv} t/\tan(\gamma) \qquad (8)$$

The value of $h_1$ may then be determined by subjecting the heater element to the fluid of interest at atmospheric pressure and substantially zero flow, thereby reducing $h_2$ to zero. A time lag can then be measured between the input signal and the output signal of the heater element under atmospheric pressure. The value of $h_1$ can then be calculated using the relation:

$$h_1 = [-2\pi f c_{pv} t/\tan(\gamma)] - h_3 \qquad (9)$$

where $h_3$ is known from equation (8).

Finally, the value of $h_2$ may be determined by subjecting the heater means to the fluid of interest at a predetermined non-zero flow rate. A time lag can then be measured between the input signal and the output signal of the heater means under the non-zero flow condition. The value of $h_2$ can then be calculated using the relation:

$$h_2 = [-2\pi f c_{pv} t/\tan(\gamma)] - h_1 - h_3 \qquad (10)$$

where $h_2$ and $h_3$ are known from equations (8) and (9) above.

In the illustrative embodiment shown in FIG. 7, the heater element 250 and the support member 252 have a composite specific heat value, $c_{pv}$. Further, the heater element 250 has a coefficient of conductive heat transfer to the substrate 254, $h_3$. Once these parameters are determined, for example by prior calibration as described above, the thermal conductivity, k, of the fluid of interest can be determined at substantially zero flow, after determining L, via a fluid of known k, by using the relation:

$$k = (-2\pi f c_{pv} t/\tan(\gamma) - h_3) L_1 \qquad (11)$$

Figure 10:
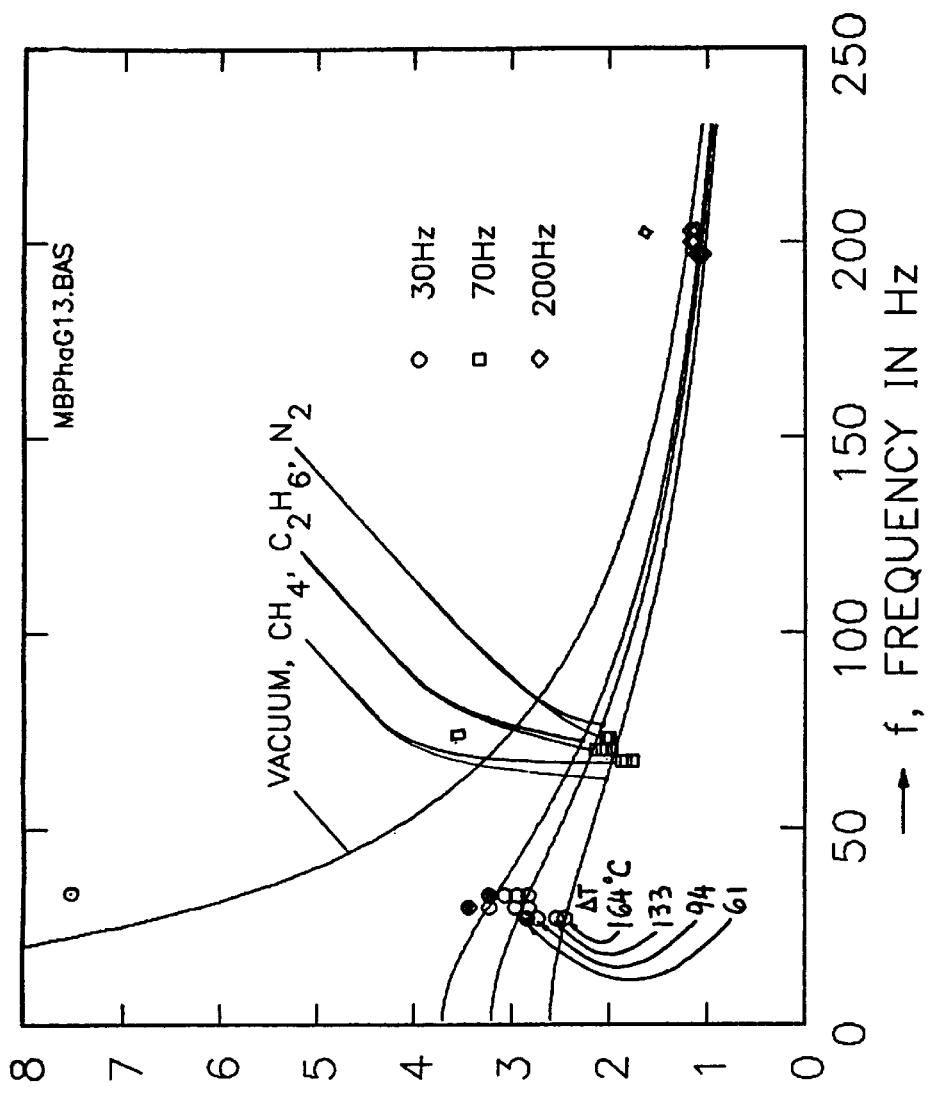
FIG. 10 is a graph showing the phase lag $\Delta z_{k,p}$ versus the frequency of the input signal for various gas compositions.
Figure 11:
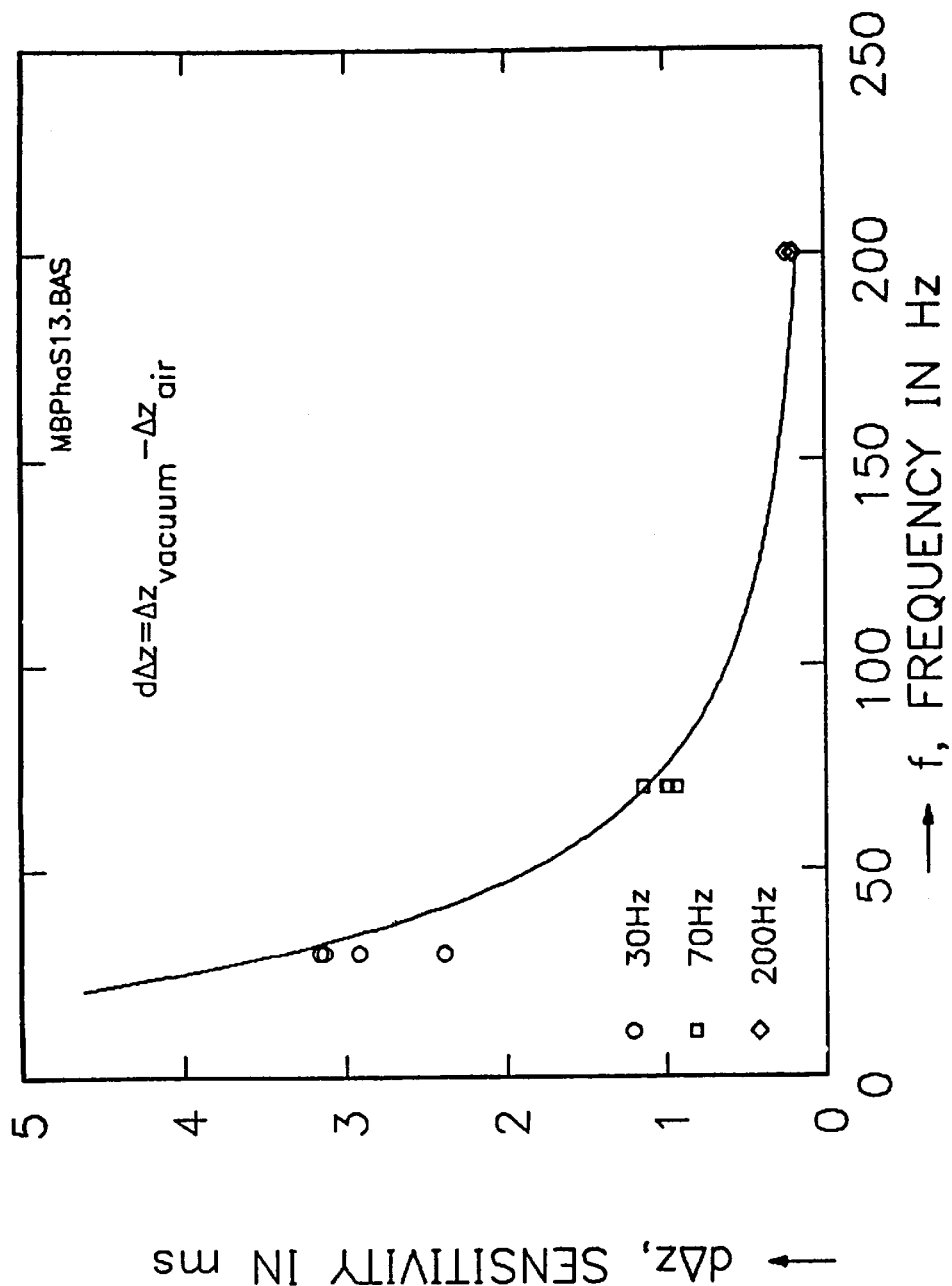
FIG. 11 is a graph showing the sensitivity of the phase lag $\Delta z_{k,p}$ versus the frequency of the input signal.

FIG. 10 is a graph showing the phase lag $\Delta z_{k,p}$ versus the frequency of the input signal for various gases including methane, ethane and nitrogen that have thermal conductivities of 81.100, 50.691, and 61.908 μcal/(sKcm), respectively, at 25° C. Three frequencies for the input signal are shown including 30, 70 and 200 Hz, and four input power levels are shown corresponding to steady state temperatures of 63, 94, 133 and 164° C. As can be seen, the time lag Δz between gases, and thus the sensitivity of thermal conductivity, k, decreases with the frequency of the input signal. This is more clearly shown in FIG. 11. Thus, the frequency for the input signal should be chosen to provide adequate sensitivity for a given sensor application.

Figure 12:
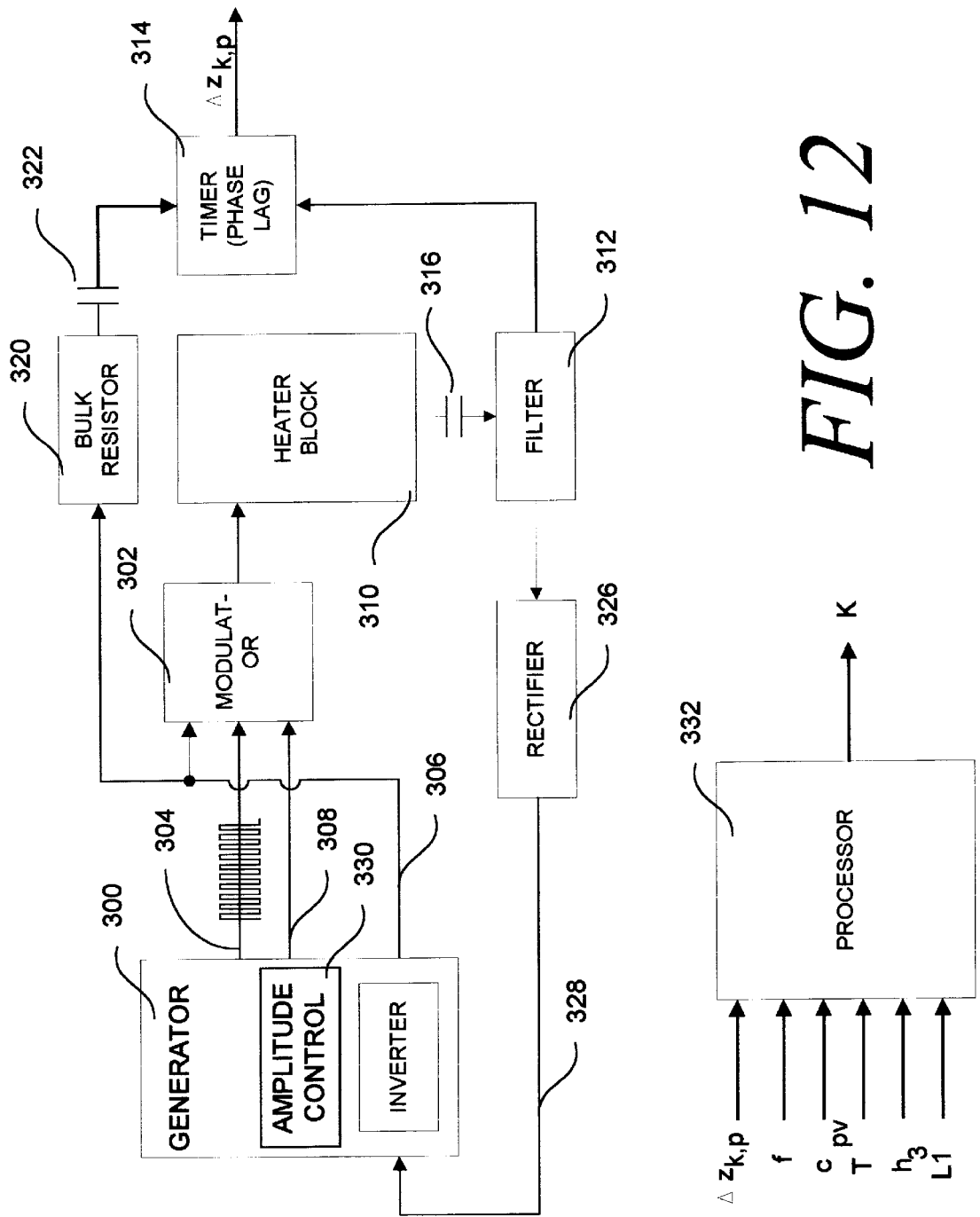
FIG. 12 is a block diagram showing another illustrative embodiment of the present invention for obtaining $\Delta z_{k,p}$.

FIG. 12 is a block diagram showing another illustrative embodiment of the present invention for obtaining $\Delta z_{k,p}$. In this embodiment, it is contemplated that the input signal may include both a high frequency component and a lower frequency component. The lower frequency component preferably modulates the high frequency component. This construction allows an accurate dosage of power to be delivered to the heater element, while eliminating frequency doubling effects that may occur without adding a DC component to the input signal. The high frequency component is preferably in the range of 0.1 to 3 MHz, while the lower frequency component is preferably in the range of 30 to 200 Hz.

Figure 13:
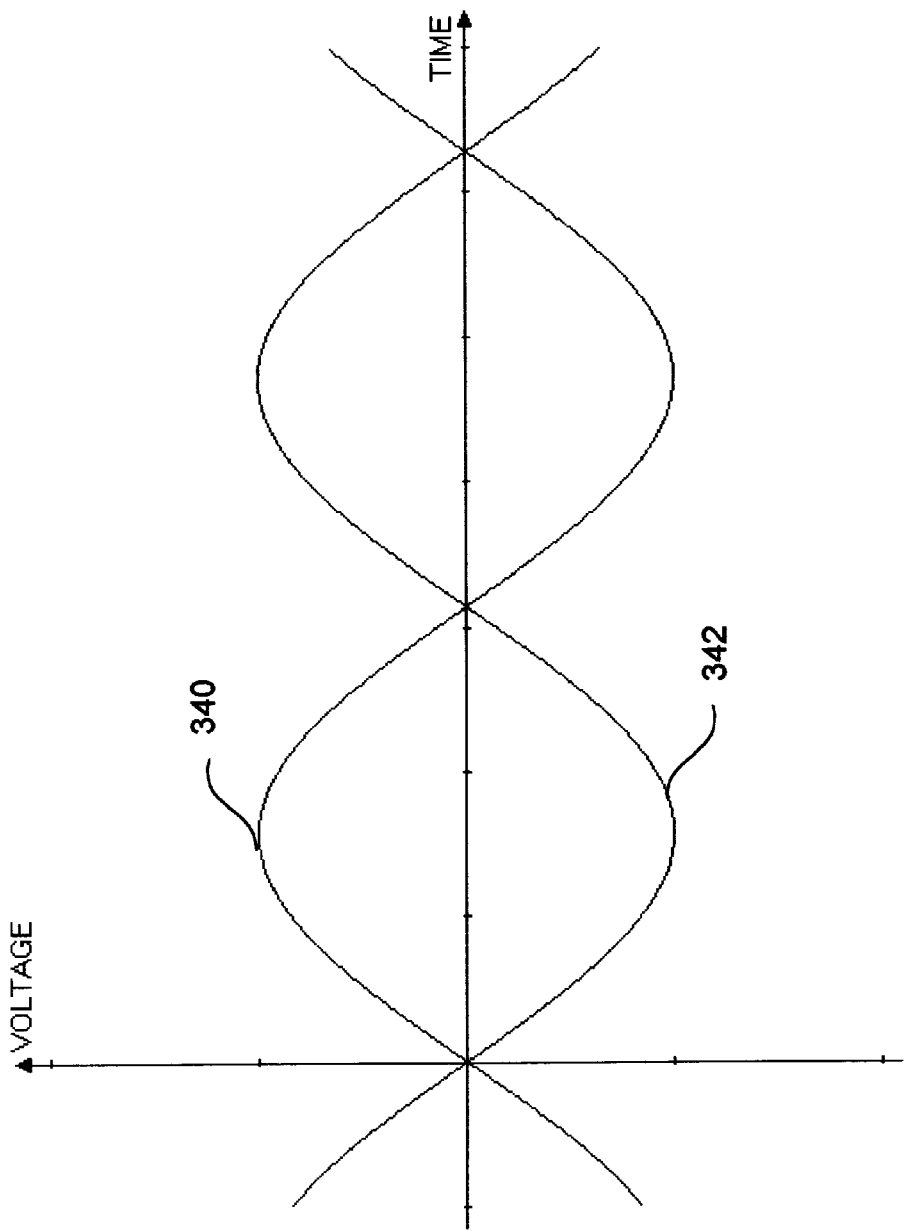
FIG. 13 is a timing diagram showing the desired input signal and a inverted copy thereof.
Figure 14:
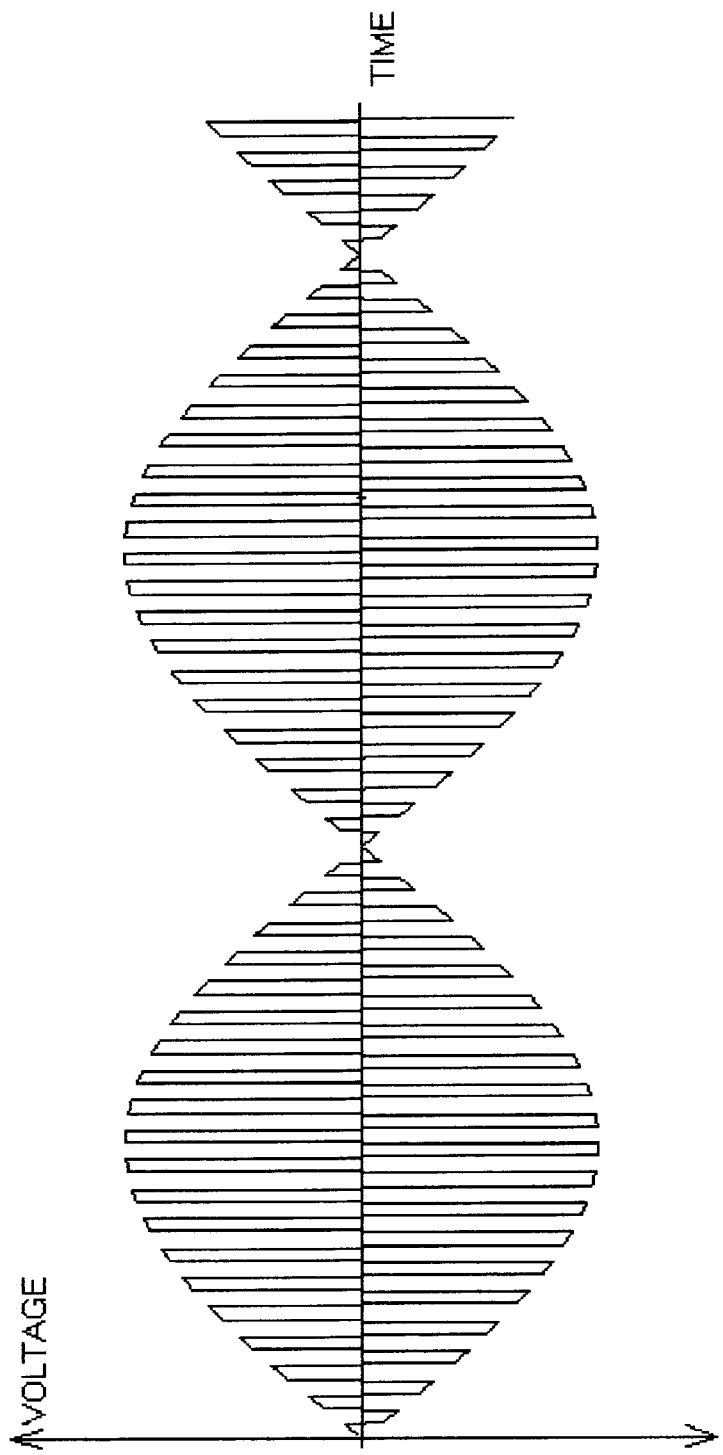
FIG. 14 is a timing diagram showing a high frequency signal modulated by the desired input signals of FIG. 13.
Figure 15:
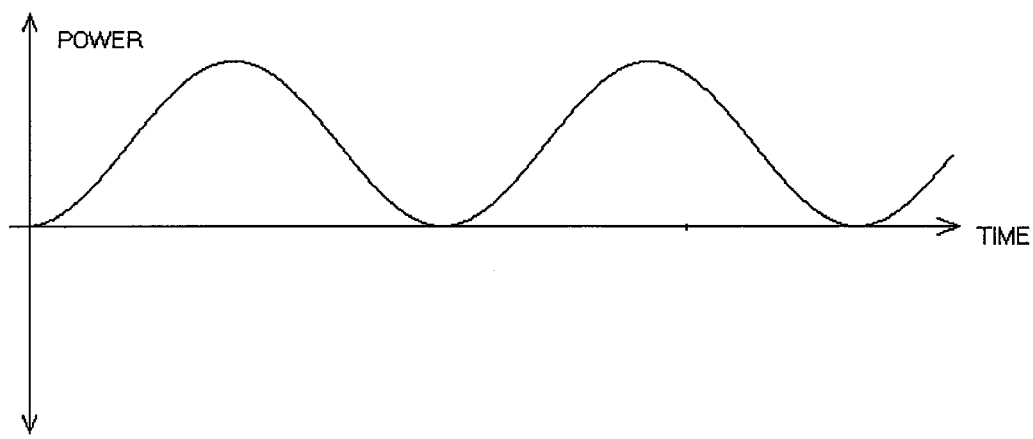
FIG. 15 is a timing diagram showing the power of the modulated input signal of FIG. 14, which is provided to the heater element.

A generator 300 generates and provides the high frequency component of the input signal to a modulator 302 via interface 304. The generator 300 also generates the lower frequency component, and an inverted copy thereof, and provides these signals to modulator 302 via interfaces 306 and 308, respectively. An illustrative lower frequency component 340 and inverted copy thereof 342 are shown in FIG. 13. The modulator 302 modulates the high frequency component using the lower frequency component signals to produce a modulated heater input signal. An illustrative modulated heater input signal is shown in FIG. 14. The power delivered by the modulated heater input signal is shown in FIG. 15.

The modulated heater input signal is provided to heater block 310. To simultaneously provide power to, and measure the resistance response of the heater element, the heater element is preferably provided in one leg of a Wheatstone bridge, for example as shown in FIG. 8. Thus, in the illustrative embodiment, the heater block 310 of FIG. 12 preferably includes a circuit similar to that shown in FIG. 8.

Figure 16:
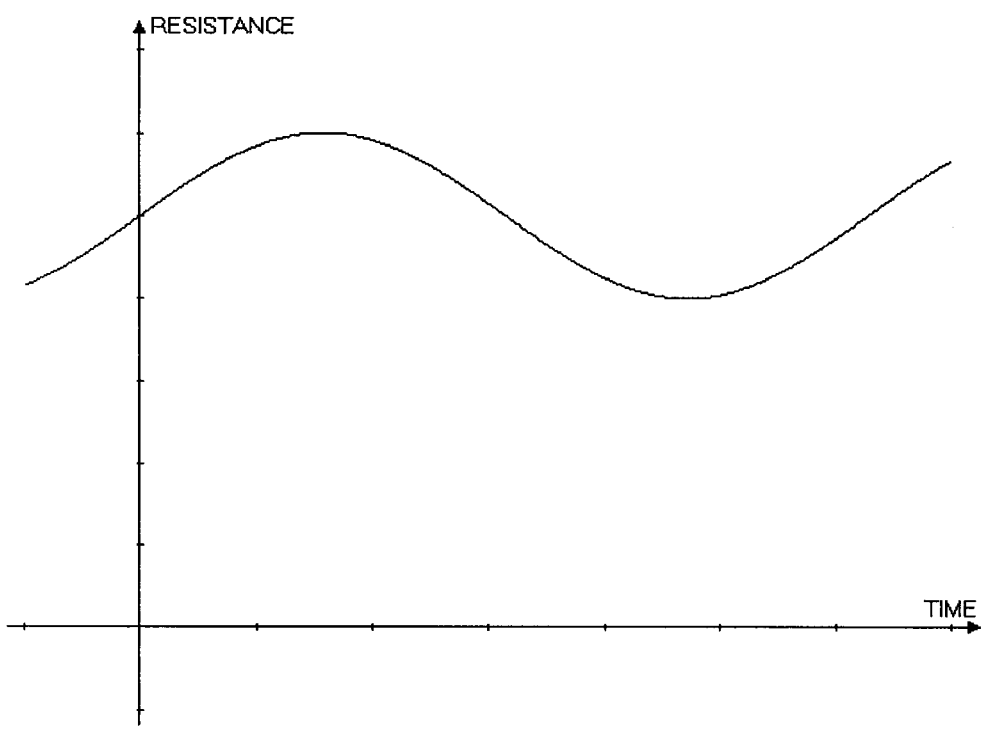
FIG. 16 is a timing diagram showing the resistance of the heater element versus time when the power signal of FIG. 15 is provided thereto.

The modulated heater input signal is provided to a power input terminal of the Wheatstone bridge, such as power input terminal 264 of FIG. 8, which is either directly or indirectly coupled to the heater element. In this configuration, the Wheatstone bridge provides a differential output signal with an amplitude that is proportional to the resistance of the heater element. The differential output of the Wheatstone bridge may be provided to a differential amplifier, as shown in FIG. 8, or may be directly provided as the output of heater block 310. An illustrative transient resistance response of the heater element is shown in FIG. 16.

For accurate measurement of the heater resistance, the high frequency component may be removed from the output signal of the Wheatstone bridge using any number of techniques. One such technique is to provide a low-pass filter 312 at the output of the heater block 310 which allows only the lower frequency component of the output signal to pass. The resulting filtered signal may then be provided to a stop input of a high frequency timer 314. Preferably, the output signal of the heater block 310 is AC coupled to the filter 312, as shown by capacitor 316. The filter 312 may provide the AC coupling function, or a separate element such as capacitor 316 may be provided.

The start input of the high frequency timer 314 may be coupled to the lower frequency component of the input signal. More preferably, however, the lower frequency component of the input signal is coupled to the start input of the high frequency timer 314 via a bulk resistor 320 and a capacitor 322 as shown. Bulk resistors feature minimal phase lag due to their strong coupling (high $h^3$-value). Capacitor 322 AC couples the lower frequency component of the input signal to the start input of the high frequency timer 314.

Because both the input signal and the output signal are AC coupled to the timer start and stop inputs, respectively, the zero crossing points of the input and output signals may be used to trigger the high frequency timer 314. This allows the time lag measurement of the high frequency timer 314 to be relatively independent of the amplitudes of the input and output signals, thereby increasing the accuracy of the measurement.

As can be seen from the above description, high frequency timer 314 starts when the AC coupled lower frequency component of the input signal crosses some predefined threshold, preferably zero. Likewise, high frequency timer 314 stops when the AC coupled output signal, which represents the resistance of the heater element, crosses some predefined threshold, preferably zero. FIG. 9 shows the resulting time lag $\Delta z_{k,p}$ determined by the high frequency timer 314. Processor 332 then uses the time lag $\Delta z_{k,p}$, along with f, $c_{p,v}$, t, $h_3$ and L, to calculate the thermal conductivity, k, using the relation shown in Equation 11 above.

In some applications, it may be desirable to control the amplitude of the transient elevated temperature condition of the heater element. This is preferably accomplished by providing an amplitude control signal that is indicative of the amplitude of the resistance change in the heater element. The amplitude control signal may be provided by a rectifier 326, which rectifies the filtered output signal as shown. The generator 300 may include an amplitude control block 330, which accepts the amplitude control signal via interface 328, and adjusts the amplitude of the lower frequency component and the inverted copy thereof such that the amplitude of the resistance change in the heater element remains at a relatively constant level.

Figure 17:
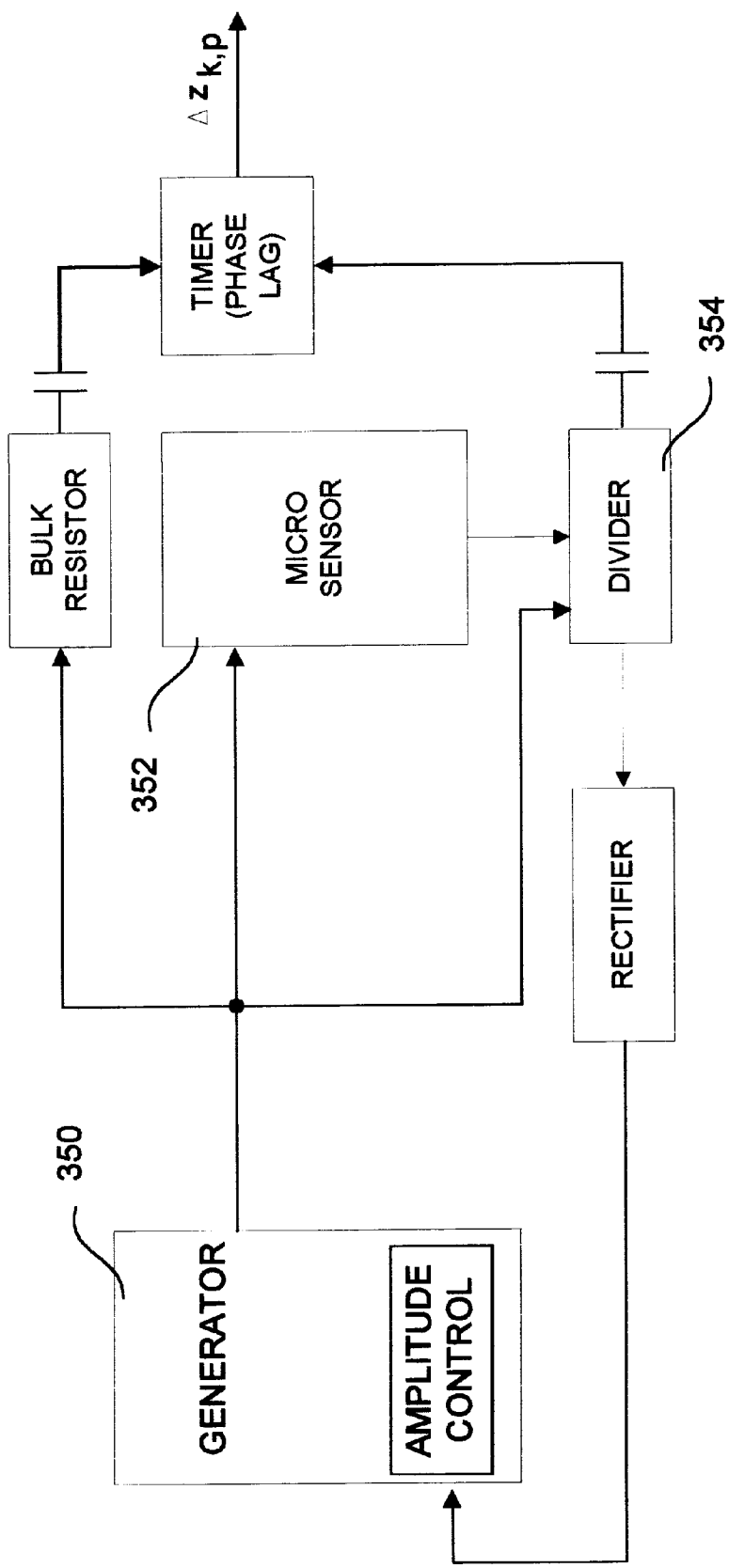
FIG. 17 is a block diagram showing yet another illustrative embodiment of the present invention for obtaining $\Delta z_{k,p}$.

FIG. 17 is a block diagram showing yet another illustrative embodiment of the present invention for obtaining $\Delta z_{k,p}$. In this approach, the generator 350 only provides the lower frequency component to the heater element, with or without a DC offset depending on whether frequency doubling is desired. As with the previous embodiment, the time varying input signal is provided to a power input terminal of a Wheatstone bridge in heater block 352. To remove the effect of the time-varying input signal from the output signal of the Wheatstone bridge, an analog divider 354 may be provided. The analog divider 354 divides the output signal of the Wheatstone bridge by the input signal. This may help reduce the influence of the time-varying input signal on the output signal. The remaining portions of the embodiment shown in FIG. 17 operate similar to that described with reference to FIG. 12.

While the above description has primarily been directed toward obtaining the thermal conductivity, k, of a fluid of interest, it is contemplated that similar apparatus and methods may be used to determine other fluid properties including temperature and pressure. For example, if thermal conductivity curves of the fluid of interest are known versus temperature and/or pressure, then the time lag $\Delta z_{k,p}$ can be used to determine the temperature and/or pressure of the fluid. This may be accomplished by: (1) measuring $\Delta z_{k,p}$ and calculating a thermal conductivity therefrom as described above; and (2) relating the so obtained thermal conductivity value to the pressure and/or temperature of that fluid, for which its pressure and temperature dependence of k has been determined beforehand or elsewhere. The measured $k_m$-value may differ from the literature value of k(T,p) if the influence of the mean-free path and container/cavity size are not taken into account, especially at low pressures, but this may be precisely the sought pressure-effect when this device is used in a mode known as the Pirani pressure sensor.

Having thus described the preferred embodiments of the present invention, those of skill in the art will readily appreciate that the teachings found herein may be applied to yet other embodiments within the scope of the claims hereto attached.

What is claimed is:

1. Apparatus for determining selected properties of a fluid of interest at substantially zero flow, comprising:

heater means in thermal communication with the fluid of interest, said heater means having a resistance that changes with temperature;

energizing means connected to said heater means for energizing said heater means, said energizing means providing a periodic time-varying input signal to said heater means to induce a transient elevated temperature condition in said heater means;

output means for providing an output signal that is a function of the resistance of said heater means;

time lag means for determining a time lag between the input signal and the output signal during the transient elevated temperature condition; and determining means for determining the selected properties of the fluid of interest using the time lag.

2. Apparatus according to claim 1 wherein said output means comprises a Wheatstone bridge having four legs, said heater means incorporated into one of the four legs of the Wheatstone bridge.

3. Apparatus according to claim 2 wherein said Wheatstone bridge has a power input terminal, said input signal provided to the power input terminal of the Wheatstone bridge.

4. Apparatus according to claim 3 wherein the Wheatstone bridge provides a differential output signal with an amplitude that is proportional to the resistance of said heater means.

5. Apparatus according to claim 4 wherein said input signal comprises a first signal having a first frequency that is modulated by a second signal having a second frequency, wherein the first frequency is higher than said second frequency.

6. Apparatus according to claim 5 wherein the differential output signal is provided to a filter, said filter filtering out said first signal from the differential output signal and converting the result to an AC coupled output signal centered approximately about ground.

7. Apparatus according to claim 6 wherein said time lag means comprises a digital counter having a start input and a stop input, said start input being electrically responsive to said second signal and said stop input being electrically responsive to said AC coupled output signal.

8. Apparatus according to claim 7 further comprises a amplitude control means, said amplitude control means providing a control signal that is indicative of the amplitude of the resistance change in said heater means.

9. Apparatus according to claim 8 wherein said energizing means receives the amplitude control signal, and adjusts the periodic time-varying input signal such that the amplitude of the resistance change in said heater means remains relatively constant.

10. Apparatus according to claim 9 wherein said amplitude control means comprises a rectifier.

11. Apparatus according to claim 4 further comprising a divider means, said divider means dividing the differential output signal and the input signal, and providing an AC coupled output signal.

12. Apparatus according to claim 11 wherein said time lag means comprises a counter having a start input and a stop input, said start input being electrically responsive to said input signal and said stop input being electrically responsive to said AC coupled output signal.

13. Apparatus according to claim 1 wherein said heater means comprises a wire.

14. Apparatus according to claim 1 wherein said heater means comprises a film.

15. Apparatus according to claim 14 wherein said film is positioned on a support member.

16. Apparatus according to claim 15 wherein said film is formed from platinum, and said support member is formed from $Si_3N_4$.

17. Apparatus according to claim 15 wherein said film and said support member have a specific (volumetric) heat value, $c_{pv}$.

18. Apparatus according to claim 17 wherein said support member is attached to a substrate, and said heater means has a coefficient of conductive heat transfer to the substrate, $h_3$.

19. Apparatus according to claim 18 wherein said determining means determines the thermal conductivity, k, of the fluid of interest based on the relation:

$$k=(-2\pi f c_{pv} t/\tan(\gamma)-h_3)L_1$$

where, $h_3$=coefficient of conductive heat transfer to the substrate, $c_{pv}$=specific heat per unit volume for the combined heater film and support member, t=thickness of the heater film, $L_1$=characteristic length of thermal conduction from the heater means into the fluid phase, $\Delta z$=time lag between input signal and the resistance of the heater means, $\gamma$=phase lag between input signal and the resistance of the heater means ($\gamma=\Delta z \cdot 2\pi f$).

20. Apparatus according to claim 1 wherein said periodic time-varying input signal is a sine wave.

21. Apparatus according to claim 1 wherein said periodic time-varying input signal is a square wave.

22. Apparatus according to claim 1 wherein said periodic time-varying input signal is a triangle wave.

23. A method for determining the thermal conductivity, k, of a fluid of interest, comprising:

energizing a heater means with a periodic time-varying input signal to induce a transient elevated temperature condition in said heater means, said heater means being in thermal communication with the fluid of interest and having a resistance that varies with temperature;

determining a time lag between the input signal and the time varying resistance of said heater means during the transient elevated temperature condition; and determining k of the fluid of interest using the time lag.

24. A method according to claim 23 wherein said heater means comprises a thin film having a thickness t.

25. A method according to claim 24 wherein said thin film is positioned on a support member.

26. A method according to claim 25 wherein said thin film and said support member have a composite or average volumetric specific heat value, $c_{pv}$.

27. A method according to claim 26 wherein said support member is attached to a substrate, and said heater means has a coefficient of conductive heat transfer to the substrate, $h_3$.

28. A method according to claim 27 wherein said heater means has a coefficient for conductive heat transfer $h_1$ to the fluid of interest.

29. A method according to claim 28 wherein said heater means has a coefficient for forced convective heat transfer, $h_2$, to the fluid of interest under laminar flow.

30. A method according to claim 29 further comprising the steps of:

determining the value of $h_2$; and determining the value of $h_3$.

31. A method according to claim 30 wherein the value of $h_3$ is determined by:

subjecting the heater means to a vacuum, thereby reducing $h_1$ and $h_2$ to zero;

determining a time lag between the input signal and the time varying resistance of said heater means during the transient elevated temperature condition; and calculating $h_3$ based on the relation:

$$h_3 = -2\pi f c_{pv} t / \tan(\gamma)$$

where, $\gamma$=phase lag between the input signal and the resistance of the heater means under a vacuum.

32. A method according to claim 31 wherein the value of $h_1$ is determined by:

subjecting the heater means to the fluid of interest at atmospheric pressure and substantially zero flow, thereby reducing $h_2$ to zero;

determining a time lag between the input signal and the time varying resistance of said heater means during the transient elevated temperature condition; and calculating $h_1$ based on the relation:

$$h_1 = [-2\pi f c_{pv} t / \tan(\gamma)] - h_3$$

where, $h_3$=the value of $h_3$ determined in claim 31, $\gamma$=phase lag between input signal and the resistance of the heater means with zero flow.

33. A method according to claim 32 wherein the value of $h_2$ is determined by:

subjecting the heater means to the fluid of interest at a predetermined non-zero flow rate;

determining a time lag between the input signal and the time varying resistance of said heater means during the transient elevated temperature condition; and calculating $h_2$ based on the relation:

$$h_2 = [-2\pi f c_{pv} t / \tan(\gamma)] - h_1 - h_3$$

where, $h_3$=the value of $h_3$ determined in claim 31, $h_1$=the value of $h_1$ determined in claim 32, $\gamma$=phase lag between input signal and the resistance of the heater means with a predetermined non-zero flow rate.

34. A method according to claim 30 further comprising the step of calculating the thermal conductivity, k, of the fluid of interest based on the relation:

$$k = (-2\pi f c_{pv} t / \tan(\gamma) - h_3) L_1$$

where, $h_3$=coefficient of conductive heat transfer to the substrate $c_{pv}$=specific heat per unit volume for the heater film and support member, t=thickness of the heater film, $L_1$=characteristic length of thermal conduction from the heater means into the fluid phase, $\Delta z$=time lag between input signal and the resistance of the heater means, $\gamma$=phase lag between input signal and the resistance of the heater means ($\gamma = \Delta z \cdot 2\pi f$).

35. A method for determining a selected fluid property of a fluid of interest, comprising:

energizing a heater means with a periodic time-varying input signal to induce a transient elevated temperature condition in said heater means, said heater means being in thermal communication with the fluid of interest and having a resistance that varies with temperature;

determining a time lag between the input signal and the time varying resistance of said heater means during the transient elevated temperature condition; and determining the selected fluid property of the fluid of interest using the time lag.

* * * * *